(12) United States Patent
Polinelli et al.

(10) Patent No.: US 7,404,217 B2
(45) Date of Patent: Jul. 29, 2008

(54) SCREEN FOR EYE PROTECTION GOGGLES AND A METHOD OF FORMING A SCREEN

(75) Inventors: Riccardo Polinelli, Galliate Lombardo (IT); Paolo Pavanello, Carnago (IT)

(73) Assignee: Spy Optic, Inc., Carlsbad, CA (US)

( * ) Notice: Subject to any disclaimer, the term of this patent is extended or adjusted under 35 U.S.C. 154(b) by 81 days.

(21) Appl. No.: 11/218,743

(22) Filed: Sep. 2, 2005

(65) Prior Publication Data

US 2006/0200895 A1    Sep. 14, 2006

(30) Foreign Application Priority Data

Oct. 29, 2004    (IT)    .................... MI2004A2082

(51) Int. Cl.
*A61F 9/02*    (2006.01)
(52) U.S. Cl. .......................................... 2/435
(58) Field of Classification Search ...... 2/435
See application file for complete search history.

(56) References Cited

U.S. PATENT DOCUMENTS

| | | | |
|---|---|---|---|
| 2,526,737 A | 10/1950 | Farina | |
| 2,665,686 A | 1/1954 | Wood | |
| 3,012,248 A | 12/1961 | Kleinman | |
| 3,377,626 A | 4/1968 | Smith | |
| 3,395,406 A | 8/1968 | Smith | |
| 3,591,864 A * | 7/1971 | Allsop | 2/436 |
| 3,718,937 A * | 3/1973 | Smith | 2/436 |
| 3,825,953 A | 7/1974 | Hunter | |
| 4,011,595 A | 3/1977 | Shields | |
| 4,149,276 A | 4/1979 | Castro | |
| 4,290,673 A | 9/1981 | Yamamoto | |
| 4,334,941 A | 6/1982 | Neely, Jr. | |
| 4,373,788 A | 2/1983 | Herbert | |
| 4,414,693 A | 11/1983 | Brody | |
| 4,443,893 A | 4/1984 | Yamamoto | |
| 4,446,184 A | 5/1984 | Bowser | |
| 4,556,995 A | 12/1985 | Yamamoto | |
| 4,571,748 A | 2/1986 | Carroll et al. | |
| 4,682,007 A | 7/1987 | Hollander | |
| 4,689,838 A | 9/1987 | Angermann et al. | |
| 4,707,863 A | 11/1987 | McNeal | |
| 4,989,274 A | 2/1991 | Patelski, III | |
| 5,018,223 A | 5/1991 | Dawson et al. | |
| 5,073,324 A | 12/1991 | Beaudet | |
| 5,162,825 A | 11/1992 | Kamekura et al. | |

(Continued)

FOREIGN PATENT DOCUMENTS

AT    406448 B    3/1998

(Continued)

*Primary Examiner*—Katherine Moran
(74) *Attorney, Agent, or Firm*—Stetina Brunda Garred & Brucker

(57) ABSTRACT

A screen for eye protection goggles is disclosed having a first and a second lens (5, 6) connected together; the screen (3) being characterized by including a seal (7) that extends along a closed ring-shaped path and is positioned along the rims (13, 15) of the first and the second lenses (5, 6) in such a way as to join the first and the second lens (5, 6) and form an airtight cavity (8) between the first and the second lens (5, 6).

6 Claims, 2 Drawing Sheets

U.S. PATENT DOCUMENTS

| | | | |
|---|---|---|---|
| 5,182,817 A | 2/1993 | Branum | |
| 5,319,397 A | 6/1994 | Ryden | |
| 5,339,119 A | 8/1994 | Gardner | |
| 5,352,532 A | 10/1994 | Kline | |
| 5,363,512 A | 11/1994 | Grabos et al. | |
| 5,421,037 A | 6/1995 | Schulze | |
| 5,428,411 A * | 6/1995 | Kopfer | 351/62 |
| 5,495,623 A | 3/1996 | Leonardi | |
| 5,542,130 A | 8/1996 | Grabos et al. | |
| 5,642,530 A * | 7/1997 | Parks | 2/435 |
| 5,652,965 A | 8/1997 | Crooks | |
| 5,682,621 A | 11/1997 | Park | |
| 5,689,834 A | 11/1997 | Wilson | |
| 5,694,650 A | 12/1997 | Hong | |
| 5,802,622 A | 9/1998 | Baharad et al. | |
| 5,890,237 A | 4/1999 | Herman | |
| 5,949,514 A | 9/1999 | Wargon | |
| 5,966,746 A | 10/1999 | Reedy | |
| 6,009,564 A | 1/2000 | Tackles et al. | |
| 6,038,707 A | 3/2000 | Ryden et al. | |
| 6,049,917 A | 4/2000 | Ryden | |
| 6,065,833 A | 5/2000 | Tiano et al. | |
| 6,092,895 A | 7/2000 | Sato et al. | |
| 6,098,204 A | 8/2000 | Arnette | |
| 6,105,177 A | 8/2000 | Paulson et al. | |
| 6,138,285 A | 10/2000 | Robrahn et al. | |
| 6,224,206 B1 | 5/2001 | Schwartz | |
| 6,253,387 B1 | 7/2001 | Yu | |
| 6,276,795 B1 | 8/2001 | Hall et al. | |
| 6,282,728 B1 * | 9/2001 | Baragar et al. | 2/428 |
| 6,341,863 B1 | 1/2002 | Chen-Lieh | |
| 6,405,373 B1 | 6/2002 | Grau | |
| 6,530,659 B1 | 3/2003 | Marcum | |
| 6,601,240 B2 * | 8/2003 | Tsubooka | 2/436 |
| 6,611,966 B1 | 9/2003 | Yamamoto et al. | |
| 6,637,877 B1 | 10/2003 | Hartley et al. | |
| 6,704,944 B2 | 3/2004 | Kawainshi et al. | |
| 6,705,719 B2 | 3/2004 | Grau et al. | |
| 6,713,135 B2 | 3/2004 | Gibbons et al. | |
| 6,772,448 B1 * | 8/2004 | Hockaday et al. | 2/435 |
| 6,891,681 B2 | 5/2005 | Schindele | |
| 6,922,850 B1 | 8/2005 | Arnold | |
| 7,126,732 B2 * | 10/2006 | McNeal et al. | 2/436 |
| 2004/0221375 A1 | 11/2004 | Douglas | |

FOREIGN PATENT DOCUMENTS

| | | |
|---|---|---|
| CA | 2456476 | 8/2004 |
| DE | 3635703 | 10/1986 |
| DE | 8628009.0 | 10/1986 |
| DE | 3635703 | 4/1988 |
| DE | 29821855 U | 2/1992 |
| DE | 29501546 U | 3/1995 |
| DE | 29516680 U | 1/1996 |
| DE | 29718088 U | 12/1997 |
| DE | 29800973 U | 3/1998 |
| DE | 29800974 U | 6/1998 |
| DE | 29810827 U | 8/1998 |
| DE | 29810828 U | 8/1998 |
| DE | 29810829 U | 8/1998 |
| DE | 20112029 U | 9/2001 |
| DE | 20212399 U | 10/2002 |
| DE | 10136806 | 2/2008 |
| EP | 264821 A1 | 4/1988 |
| EP | 0504518 A1 | 9/1992 |
| EP | 0967061 | 12/1999 |
| EP | 1095577 | 5/2001 |
| GB | 524196 | 7/1940 |
| GB | 2284679 A | 6/1995 |
| JP | 9086975 | 3/1997 |
| JP | 11079797 | 3/1999 |

* cited by examiner

SCREEN FOR EYE PROTECTION GOGGLES AND A METHOD OF FORMING A SCREEN

CROSS-REFERENCE TO RELATED APPLICATIONS

This application claims priority to pending Italian Patent Application No. MI2004A002082 filed on Oct. 29, 2004, the entire contents of which is incorporated by, reference herein.

STATEMENT RE: FEDERALLY SPONSORED RESEARCH/DEVELOPMENT

Not Applicable

BACKGROUND

The present invention relates to a screen for eye protection goggles.

In particular, the invention relates to a screen for ski goggles, to which the invention will make specific reference without thereby excluding more general reference.

Ski goggles consist of a frame able to fit closely onto a user's face, an elastic strap connected to the frame and a transparent screen fitted onto the frame.

The function of ski goggles is to protect the user's eyes from snowflakes, dust and the flow of air generated by wind and/or the forward movement of the skier himself and at the same time to guarantee good visibility even in bad weather conditions.

Ski goggles differ from glasses by the fact that they insulate part of the face around the user's eyes in order to avoid wind, dust and snowflakes coming into contact with the eyes and irritating them or forcing the user to close his eyes while skiing. In other words, goggles, when during use they fit closely to the user's face, form a chamber that is substantially closed and insulated from the external environment.

When practicing sport, the skier perspires due to the exertion he makes his body undergo and, consequently, vapour generated by perspiration is trapped inside the closed chamber and condenses on the inside face of the screen. So the screen mists up and visibility is considerably reduced, sometimes even to zero.

BRIEF SUMMARY

To get round this problem, ski goggles are generally provided with lateral aeration slits. These slits are covered with a spongy material in order to allow the evacuation of vapour from the said chamber and, at the same time, to prevent the passage of air, dust and snowflakes from the outside. Although these openings prevent the build-up of excess pressure in the closed chamber they have proved inadequate for getting round the problem of the screen misting up.

To get round the problem of the screen misting up, a new type of goggles has been produced provided with a screen consisting of an internal lens and an external lens, which are fitted onto the frame so as to form a cavity. In this way, the internal lens is thermally insulated from the external lens and the vapour present in the mask only comes into contact with the warm internal lens, and contact with the cold external lens, which would bring about immediate condensation of the vapour, is prevented.

The two-lens screen combined with aeration slits has not completely resolved the problem. In fact, in certain exercise conditions condensation forms in the cavity and is deposited on the faces of the internal and external lenses. This fact is particularly troublesome because it is not possible to remove the condensation.

The scope of this invention is to produce a screen for eye protection goggles that is free from the problems of prior art and that, in particular, gets round in a simple and economical way the problem of condensation forming on the screen.

According to the present invention, a screen for eye protection goggles is produced that consists of a first and a second lens connected together; the screen being characterized by the fact that it includes a seal that extends along a ring-shaped path and is positioned along the rims of the first and second lens in such a way as to join the first and the second lens and form an airtight cavity between the first and second lens.

According to the invention, infiltration into the cavity of moist air and vapour produced by perspiration is prevented.

According to a special embodiment of this invention, the said cavity contains a dehumidified gas.

In this way condensation of any water vapour present in the air at the time the screen is being assembled is avoided.

The present invention also concerns a method for producing a screen for eye protection goggles.

According to this invention, a method is provided for producing a screen for eye protection goggles, the method arranging for connecting together a first and a second lens; the method being characterized by the fact that it joins together the first and the second lens with a seal that extends along a ring-shaped path and is positioned along the rims of the first and the second lens in which a way as to join the first and the second lens and form an airtight cavity between the first and the second lens.

BRIEF DESCRIPTION OF THE DRAWINGS

The present invention will not be described with reference to the attached drawings, which illustrate a non-limiting example of how to proceed, as follows.

DETAILED DESCRIPTION

Figure 1:
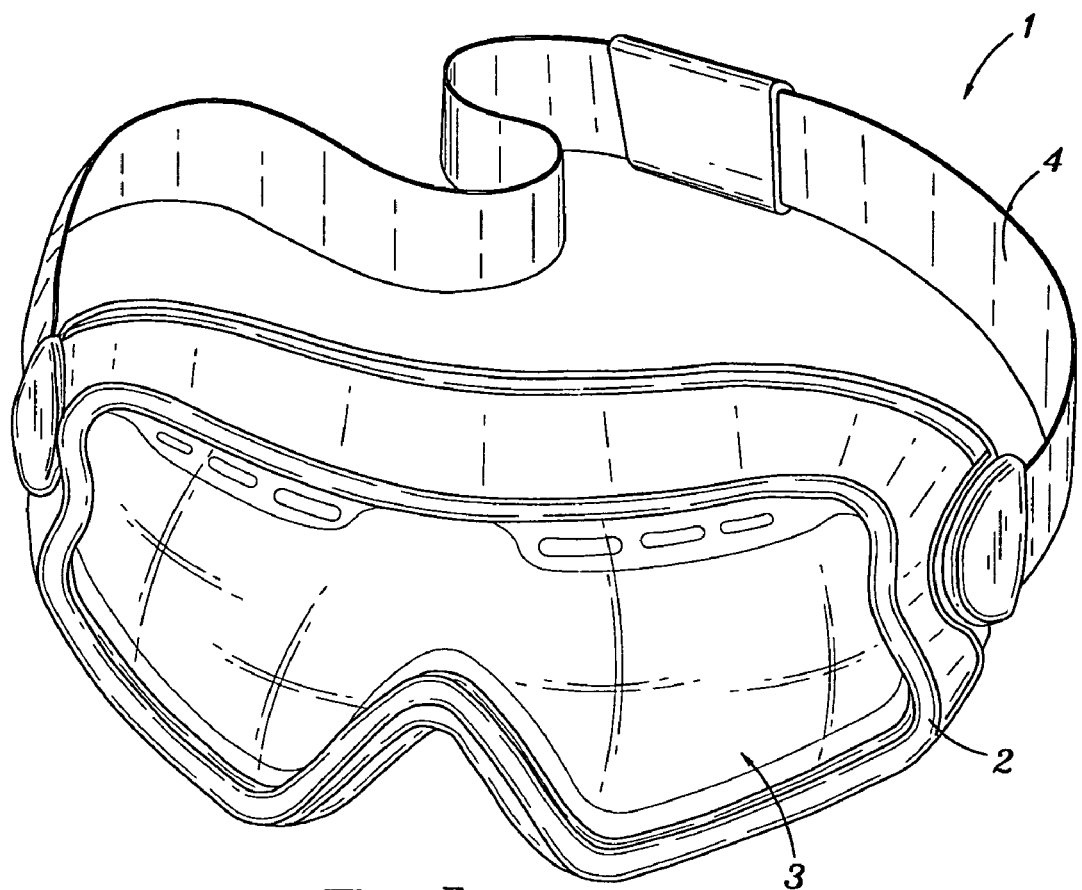
FIG. 1 is a perspective view, with parts taken away for the sake of clarity, of eye protection goggles fitted with a screen made according to the invention.

With reference to FIG. 1, 1 shows in their entirety some ski goggles suitable for being placed, when in use, on a user's face.

The goggles 1 consist of a ring shaped frame 2, a screen 3 supported by the frame 2, and an elastic strap 4 attached to the frame 2 with fastenings at opposite sides of the frame 2 itself.

Figure 3:
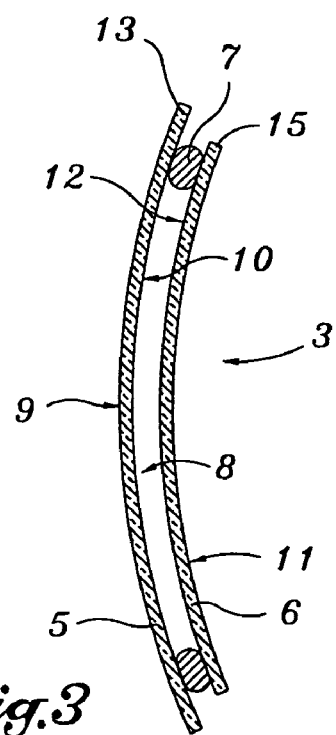
FIG. 3 is a cross-sectional view of the screen in FIG. 2, according to the cross-section lines III-III.
Figure 2:
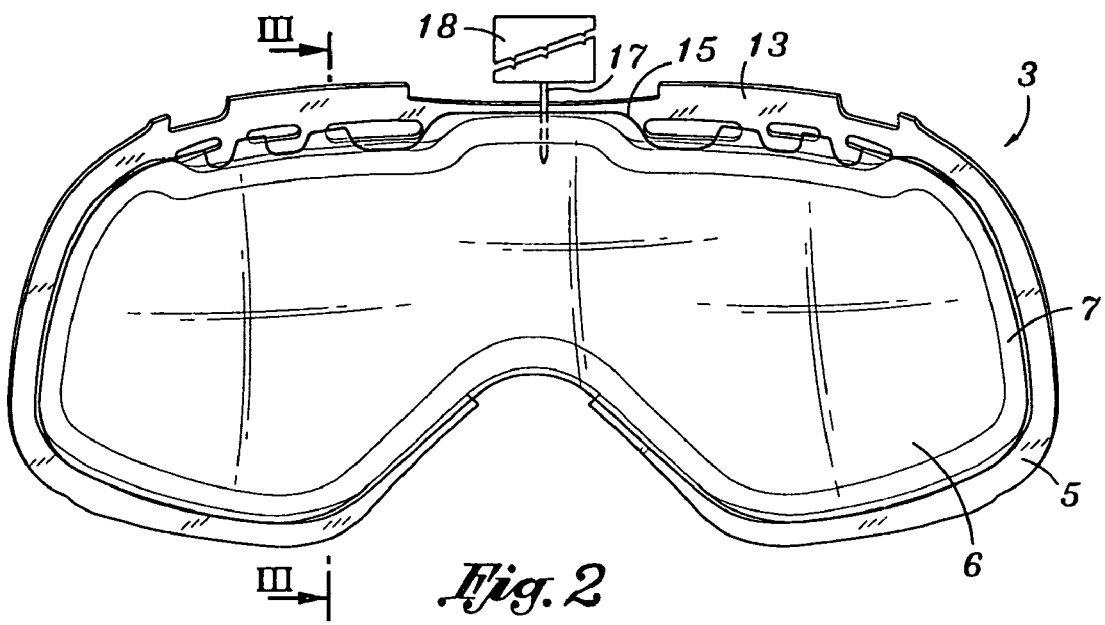
FIG. 2 is a rear elevation view of the goggles screen in FIG. 1.

With reference to FIGS. 2 and 3, the screen 3 comprises two lenses 5 and 6 joined together and held at the right distance from each other by a seal 7.

The lens 5 and 6 are spherical (alternatively they can be toroidal or cylindrical) and define an airtight cavity 8 completely insulated from the external environment. Lens 5 is defined as external insofar as it presents a face 9 that contributes towards defining the front surface of the goggles 1 and a face 10 that, to a large extent, is turned towards the cavity 8. Lens 6 is defined as internal insofar as it presents a face 11 facing, when in use, the user's face, and a face turned towards the cavity 8. Lens 5 presents a rim 13 protruding beyond the seal 7 with, at certain points, an indented profile, which is incorporated into the frame 2 and bonded to the frame 2 itself by means of slots to the frame 2 (alternatively the rim 13 is bonded to the frame 2 by means of a procedure of pressure fusion of the frame 2 itself). In the upper part of the rim 13 aeration openings 14 are present against which spongy material not illustrated in the attached figures will be positioned. Lens 6 presents a protruding rim 15 along which cuts 16 are made aligned with the openings 14.

According to an alternative embodiment not illustrated the rims 13 and 15 do not protrude from the seal 7. According to a further variant not illustrated, the openings 14 and the cuts 15 are omitted.

The seal 7 extends along a closed ring-shaped path in such a way as to completely close off any access to the cavity 8. The eternal lens 5 is made from polycarbonate, while the internal lens 6 is made with a material chosen from among polycarbonate, propionate cellulose and cellulose acetate. The seal 7 is made from rubber, preferably from a polyurethane-based or a silicon-based rubber. In both cases, the rubber is added with solvents and reticulating agents. The rubber once it has hardened has the characteristic of being self-sealing. In other words, once the rubber has hardened, if it is perforated by means of a needle or point having a small diameter it has the ability to close up again and restore the hermetic seal.

Figure 4:
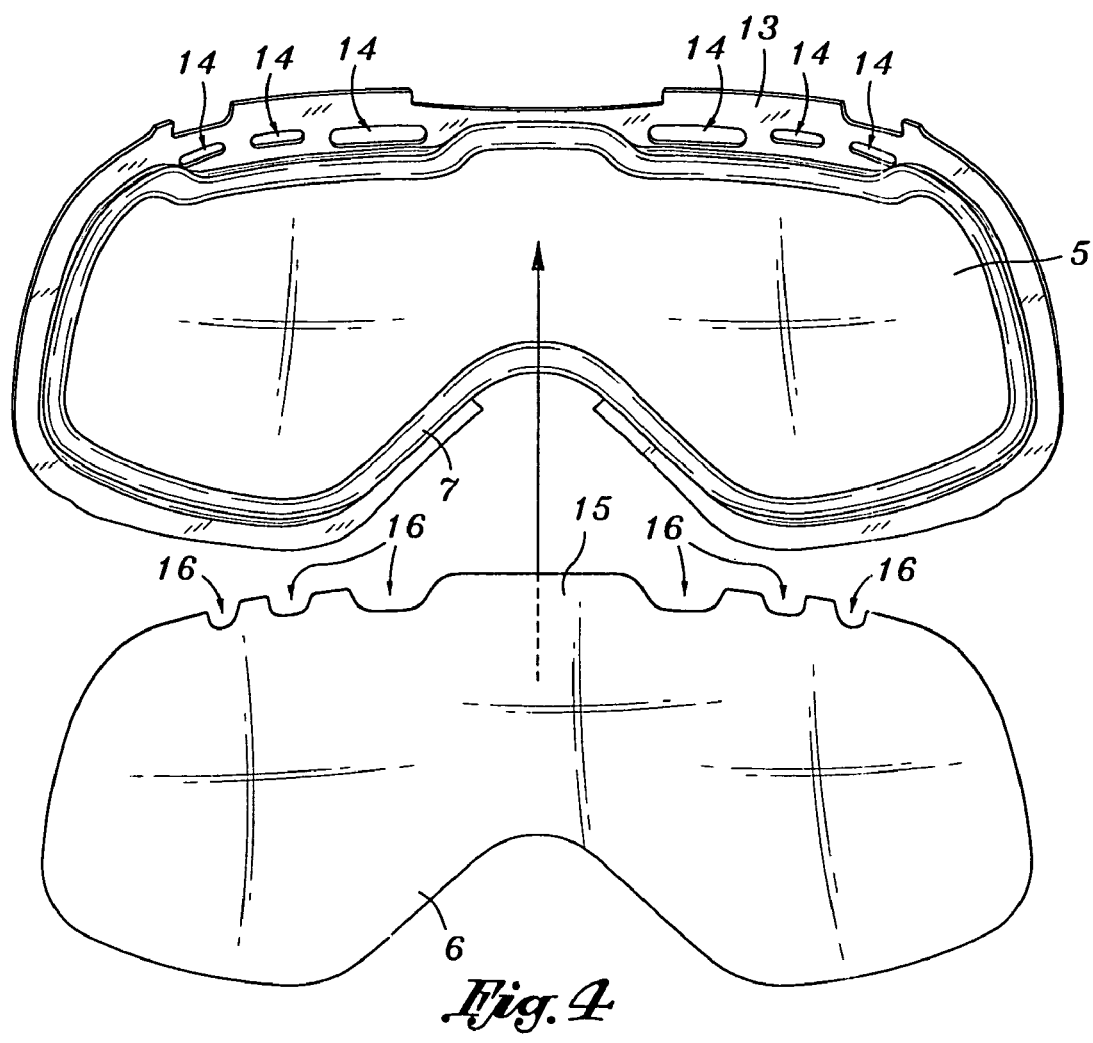
FIG. 4 is a partially exploded view of the screen in FIG. 2.

With reference to FIG. 4, once the lenses 5 and 6 have been made according to the well-known die-cutting or die-casting technologies, the method for making the screen 3 arranges for carrying out an activating treatment on the face 10 of the lens 5 along the closed ring-shaped path along which the rubber making the seal 7 will be deposited. The activating treatment has the function of modifying the molecular links and facilitating adhesion between the rubber and the polycarbonate. In the case where the internal lens 6 is also made form polycarbonate, the activating treatment is also carried out on the face 12 of the internal lens 6 only on the area intended to come into contact with the seal 7.

Next, the rubber of the seal 7 is deposited in a pasty state along the said closed ring-shaped path on the face 10 of lens 5. Lens 6 is joined to the seal 7 while this is still in a pasty state and joined, in this way, to lens 5.

Depositing the rubber in a pasty state can alternatively take place on the face 12 of lens 6, to which lens 5 will be connected.

The above-mentioned connection is carried out in a controlled environment, in other words, a dehumidified one. Once the connection has been made between lenses 5 and 6 and the seal 7 has solidified, part of the gas contained in the cavity 8 is extracted. With reference to FIG. 2, the extraction is carried out by using a needle 17 that is inserted through the seal 7, which has the ability, once the needle 17 has been extracted, to close up again hermetically the hole made by the needle 17. The gas is extracted by means of a suction device 18 in a quantity such as will bring about in the cavity 8 an absolute pressure between 700 and 900 millibars. In short, a depression is created in the cavity 8 so as to allow easy use of the goggles 1 even at high altitude. Referring to the average altitude of ski slopes, the preferred pressure in the cavity 8 is between 750 and 800 millibars, which is substantially equal to atmospheric pressure at an altitude of around 2000 meters. Without this expedient the screen 3 would be considerably distorted at high altitudes because of the predominance of pressure in the cavity compared to atmospheric pressure adversely affecting visibility to a considerable extent.

What is claimed is:

1. Method for making a screen for eye protection goggles, wherein the screen mitigates fogging due to cold temperatures and optical distortion due to changes in altitude, the method comprising the steps of:
    connecting together a first and a second lens with a seal that extends along a closed ring-shaped path and is positioned along rims of the first and the second lenses to form an airtight cavity between the first and the second lens, the connecting step comprising the steps of:
        placing the seal onto one of the first and second lenses in a pasty state along the ring shaped path; and
        connecting the first lens to the second lens with the seal being placed between them when the seal is in the pasty state;
    reducing a pressure within the airtight cavity to a pressure lower than a pressure external to the airtight cavity;
    wherein the connection of the first lens, the second lens and the seal is carried out in an environment filled with dehumidified gas.

2. Method for making a screen for eye protection goggles, wherein the screen mitigates fogging due to cold temperatures and optical distortion due to changes in altitude; the method comprising the steps of:
    connecting together a first and a second lens with a seal that extends along a closed ring-shaped path and is positioned along rims of the first and the second lenses to form an airtight cavity between the first and the second lens; and
    reducing a pressure within the airtight cavity to a pressure lower than a pressure external to the airtight cavity, the reducing step comprising the step of extracting from the cavity part of a dehumidified gas such that the pressure of the dehumidified gas is lower than a pressure external to the cavity.

3. Method according to claim 2 wherein the extracting step extracts a quantity of dehumidified gas such that an absolute pressure of the dehumidified gas is between about 700 and about 900 millibars.

4. Method according to claim 2 wherein the extracting step extracts a quantity of dehumidified gas such that an absolute pressure of the dehumidified gas is between about 750 and about 800 millibars.

5. Method according to claim 4 wherein the extracting step is carried out when the seal is in a solid state with a needle and a suction device.

6. Method according to claim 5 wherein the seal is made out of self-sealing rubber.

* * * * *